United States Patent
Lorenz et al.

(10) Patent No.: US 6,379,657 B1
(45) Date of Patent: Apr. 30, 2002

(54) COMPOSITION AND PROCESS FOR DE-COLORING DYED HAIR

(75) Inventors: Heribert Lorenz, Gross-Bieberau; Walter Eberling, Riedstadt-Crumstadt, both of (DE)

(73) Assignee: Goldwell GmbH (DE)

( * ) Notice: Subject to any disclaimer, the term of this patent is extended or adjusted under 35 U.S.C. 154(b) by 64 days.

(21) Appl. No.: 09/648,891

(22) Filed: Aug. 25, 2000

(30) Foreign Application Priority Data

Sep. 24, 1999 (DE) .......................... 199 45 877

(51) Int. Cl.$^7$ ............................... A61K 7/135
(52) U.S. Cl. ................ 424/62; 424/70.1; 424/70.22; 8/405; 132/202; 132/208
(58) Field of Search ............... 424/401, 70.1, 424/62, 70.6, 70.22; 8/405; 132/202, 208

(56) References Cited

U.S. PATENT DOCUMENTS

| 3,617,167 A | | 11/1971 | Berth et al. .................... 8/10.2 |
| 3,630,655 A | | 12/1971 | Berth et al. ....................... 8/11 |
| 3,800,809 A | | 4/1974 | Saad et al. .................... 424/62 |
| 3,892,845 A | * | 7/1975 | Cunningham et al. |
| 4,114,632 A | * | 9/1978 | Morganroth |
| 5,651,960 A | * | 7/1997 | Chan et al. |
| 6,007,585 A | * | 12/1999 | Syed et al. |
| 6,106,579 A | * | 8/2000 | Kunz et al. |

FOREIGN PATENT DOCUMENTS

| DE | 211 697 C | 9/1972 |
| DE | 26 46 435 A1 | 4/1978 |

* cited by examiner

Primary Examiner—Thurman K. Page
Assistant Examiner—Brian D. Seidleck
(74) Attorney, Agent, or Firm—Norris, McLaughlin & Marcus P.A.

(57) ABSTRACT

A composition for the decoloration of dyed hair consists of an alkaline Composition A containing at least one reducing agent and having a pH-value between 7.5 and 12.5, and a Composition B stored separately therefrom until application, having a highly acidic pH-value of 1 to 4 and containing at least one oily or fatty substance, at least one water-soluble emulsifier and at least one perfume, being present as an emulsion. Both Compositions are admixed immediately prior to application, whereby a product with a pH-value of 2.5 to 5.0 is obtained. This product can be distributed evenly on the hair without dripping, has an agreeable smell by the perfume contained and stabilized in Composition B, and effects even decoloration of the dyed hair.

8 Claims, No Drawings

COMPOSITION AND PROCESS FOR DE-COLORING DYED HAIR

BACKGROUND OF THE INVENTION

The invention concerns a composition for removing color from dyed human hair, in particular from hair which has been subject to oxidative dyeing, and a process for the application of this composition Hair colorations are very popular. In addition to temporary or semi-permanent colorations, colorations are also carried out with permanent hair dyes, produced on the basis of dyestuff precursors developed into dyes immediately prior to application with an oxidizing agent, in particular a hydrogen peroxide composition.

End-users occasionally desire to remove the color before it would fade away anyhow, or they may wish to modify their coloration. The products used for this procedure are so-called dye removers or decoloration agents mainly composed on the basis of reducing compounds.

The substances proposed for this purpose are in particular sodium dithionite, hydrogen sulfites, formaldehyde sulfoxylates such as hydroxymethane sulfonic acid, or also ascorbic acid.

Also known is a process for the decoloration of oxidatively dyed hair, wherein an acidic solution and an alkaline solution containing a reducing agent, namely hydroxymethane sulfinic acid, are mixed together immediately prior to application on the hair, the mixing producing in a solution with an acidic pH-value, which serves to remove the undesired hair coloration.

For this process it is desirable to use a high concentration of reducing agent, which, however, leads to a highly disagreeable smell.

Surprisingly, it is not possible to apply the most obvious solution to this problem, namely to add a perfume to the solution containing the reducing agent, because the perfume compositions have proven to be unstable in this solution, becoming turbid under formation of a precipitate.

SUMMARY OF THE INVENTION

The invention therefore intends to solve the problem by finding a process for the decoloring of dyed hair and a respective solution overcoming the above described disadvantages,

DESCRIPTION OF THE PREFERRED EMBODIMENTS

This solution consists in providing two Compositions A and B kept separate until application, whereby the Composition A contains at least one reducing agent, preferably in an amount from about 5% to 50% by weight in aqueous solution, having an alkaline pH-value between 7.5 and 12.5, and the Composition B consisting in an aqueous emulsion, preferable an oil-in water emulsion, comprising at least one perfume component, at least one fatty or oily component, and at least one emulsifier, the pH-value being in the highly acidic range between 1 and 4, whereby the product obtained after mixing the two Compositions has a pH-value ranging between 2.5 and 5.0.

The invention furthermore concerns a process for the decoloring of dyed hair by use of a product on colored hair obtained my mixing the above disclosed Compositions A and B.

The alkaline reducing Composition A, held separate from the acidic Composition B until application, contains as preferred reducing agent hydroxymethane sulfinic acid or the water-soluble salts thereof, preferably in an amount from about 10% to about 40%, in particular about 20% to about 40% by weight, calculated to the total composition.

Alternatively or in admixture with hydroxymethane sulfinic acid it is, however, also possible to use other reducing agents, such as sodium dithionite, alkali hydrogen sulfites or also reductones such as ascorbic acid and the salts thereof.

This Composition A preferably has a pH-value between about 8 and 12, in particular about 8.5 to 11, for example 9 to 10, and preferably comprises additional components, such as thickening agents.

The quantity and type of the reducing agent determines the precise pH-value, which can also be adjusted by direct addition of alkali.

Suitable thickening agents are, for example, cellulose derivates such as hydroxyethyl, hydroxypropyl or hydroxypropyl methyl cellulose, guar gum and the derivatives thereof, xanthan gum and the derivatives thereof, etc., the preferred amounts depending on the desired viscosity and ranging between about 0.1% to about 2.5%, in particular about 0.25% to about 2%, preferably between about 0.5% to 1.5% by weight, calculated to the total Composition A.

Composition B, having a pH-value of 1 to 4, in particular about 1.5 to 3, in addition to containing at least one, preferably organic, acid such as citric acid, tartaric acid, lactic acid, benztartaric acid, maleic acid, gluconic acid, succinic acid, glycoxy acid or glyxolic acid, comprises at least one fatty or oily compound and at least one surface-active substance as emulsifier, as well as a perfume, preferably prepared as an oil-in-water emulsion.

The amount of the acid used naturally depends on the desired pH-value of said emulsion.

The Composition B contains at least one fatty or oily compound, preferably in an amount ranging from about 0.5% to about 10%, preferably from about 1% to 7.5%, in particular about 1.5% 5% by weight, calculated to the total composition.

Suitable fatty or oily substances are, for example, $C_{10}$–$C_{24}$-fatty alcohols, in particular lauryl alcohol, myristyl alcohol, palmityl alcohol, cetyl alcohol, oleyl alcohol, stearyl alcohol, behenyl alcohol, admixtures of these alcohols with further alcohols, for example coco fatty alcohol or cetyl stearyl alcohol.

Further suitable fatty and oily substances, including waxes, are in particular natural oils, such as avocado oil, coconut oil, palm oil, sesame oil, peanut oil, whale oil, sunflower oil, almond oil, peach kernel oil, wheat germ oil, macadamia nut oil, night primrose oil, jojoba oil, castor oil, or also olive oil, soya oil, lanolin and the derivatives thereof, as well as mineral oils such as paraffin oil and petrolatum. Synthetic oils and waxes are, for example, silicone oils, polyethylene glycols, etc. Further suitable hydrophobic components are in particular fatty acid esters such as isopropyl myristate, palmitate, stearate and isostearate, oleyl oleate, isocetyl stearate, hexyl laurate, dibutyl adipate, dioctyl adipate, myristyl myristate, oleyl erucate, polyethylene glycol and polyglyceryl fatty acid esters such as PEG-7-glyceryl cocoate, cetyl palmitate, etc.

Emulsion B furthermore contains at least one emulsifier, preferably in an amount from about 0.25% to 7.5%, in particular about 0.3% to 5% by weight, calculated to the total composition. Suitable emulsifiers are known from the state of the art, see, for example, K. Schrader, "Grundlagen und Rezepturen der Kosmetika", $2^{nd}$ Ed. (1989), pp. 387–524.

Useful are in particular anionic, nonionic, amphoteric and/or zwitterionic substances.

It is self-understood that mixtures of various surface-active substances are also suitable.

Preferred are anionic emulsifiers of the sulfate, sulfonate, carboxylate and alkyl phosphate type, optionally in admixture with known nonionic and/or amphoteric (zwitterionic) surfactants, for example, the known $C_{10}$–$C_{18}$-alkyl sulfates and ether sulfates, for example, $C_{12}$–$C_{14}$-alkyl ether sulfate, lauryl ether sulfate, especially with 1 to 4 ethylene oxide groups in the molecule, furthermore monoglyceride (ether) sulfates, fatty acid amide sulfates, obtained by ethoxylation and subsequent sulfatation of fatty acid alkanolamides, and the alkali salts thereof, as well as the salts of long-chain mono- and dialkyl phosphates, which are mild, skin-compatible detergents, α-olefin sulfates or the salts thereof, alkali salts of sulfosuccinic acid semiesters, for example the disodium salt of monooctyl sulfosuccinate, alkali salts of long-chain monoalkylethoxy sulfosuccinates, alkyl polyether carboxylic acids, alkyl amido polyether carboxylic acids and $C_8$–$C_{20}$-acyl isethionates.

Useful are also $C_8$–$C_{22}$-acyl aminocarboxylic acids and the water-soluble salts thereof, such as N-lauroyl glutamate, in particular as sodium salt, N-lauroyl sarcosinate, N-$C_{12}$–$C_{18}$-acyl asparaginic acid, N-myristoyl sarcosinate, N-oleoyl sarcosinate, N-lauroyl methyl alanine, N-lauroyl lysine and N-lauroyl aminopropyl glycine, preferably in form of the water-soluble alkali or ammonium, in particular the sodium salts thereof.

Suitable nonionic surfactants are $C_8$–$C_{18}$-alkyl polyglucosides, fatty alcohol ethoxylates, sorbitan esters such as PEG-sorbitan ester, fatty acid polyglycol ester, as well as long-chain amineoxides and fatty acid alkanolamides, preferably in admixture with anionic surface-active substances.

Suitable amphoteric or zwitterionic surfactants are also known, in particular fatty acid amidoalkyl betaines, sulfobetaines, e.g., lauryl hydroxy sulfobetaine, and long-chain amino acids, such as cocoaminoacetate, cocoaminopropionate, cocoamphoacetate and -propionate, in particular in form of the alkali salts thereof.

The proportion of the perfume in the Composition B according to the invention preferably ranges from about 0.1% to 1%, in particular from about 0.2% to about 0.8% by weight, calculated to the total composition.

Useful as perfumes are all such customary compositions; according to the invention they are stabilized by the preparation as an emulsion without necessarily requiring additional use of a solubilizer; they are also compatible in the total composition, and upon application they cover the smell of the incorporated reducing agents.

Use of the composition according to the invention furthermore provides the hair with an additional conditioning effect.

The product obtained upon mixing the Compositions A and B adheres better to the hair and does not drip.

The Compositions A and in particular B can also contain further substances, in particular hair-conditioning and hair-caring substances such as cationic, nonionic, amphoteric, zwitterionic and/or anionic polymers, protein hydrolyzates, silicone derivatives, such as organopolysiloxanes, panthenol, plant extracts, lecithin, moisturizers, complexing agents, etc.

Especially suited for the final product obtained after admixture is a viscosity range between about 100 and 7,500 mPa·s, in particular about 500 to 5,000 mPa·s, measured at 20° C. in a Brookfield viscosimeter (spindle No. 4 at 20 rpm).

Although use of the composition according to the invention is mainly intended for decoloration of hair permanently dyed with oxidation hair dyes, it is self-understood that it can also be used to decolor hair semi-permanently dyed with direct-acting dyestuffs, optionally by using reducing agents in lower concentrations.

The containers holding the separately stored Compositions A and B are preferably packed as a set; they can also be filled into known two-chamber containers with a separating wall that is destroyed or removed prior to admixing. Such two chamber compartments are known as state of the art.

The procedure according to the invention is described as follows:

The oxidatively dyed hair intended for decoloration is preferably pre-treated by moistening or shampooing, then the mixture with a pH-value of 2.5 to 5.0, obtained by mixing approximately equal proportions of an alkaline reducing agent Composition A and an acid Composition B, is applied thereto, left to process for about five to thirty minutes, in particular ten to twenty minutes, rinsed off well, preferably shampooed, and optionally post-treated with an aqueous one percent to six percent, preferably two percent to three percent hydrogen peroxide solution for about 1 to 3 minutes.

The following comparison test explains the effect and advantages of the composition according to the invention by applying the process according to invention.

An alkaline Solution A, comprising

| | |
|---|---|
| 22 (g) | hydroxymethane sulfinic acid, sodium salt |
| 1 | hydroxyethyl cellulose (Natrosol ® 250MXR) |
| 77 | water (pH: 9.8) | was thoroughly mixed with an equal amount of an Emulsion B, consisting of

| | |
|---|---|
| 10.0 (g) | citric acid |
| 2.0 | cetyl stearyl alcohol |
| 0.5 | sodium lauryl sulfate |
| 0.1 | panthenol |
| 0.3 | perfume |
| 0.1 | tetra sodium-EDTA |
| 87.0 | water (pH: 1.7) |

A pleasant smelling mixture with a pH-value of 2.9 and a viscosity of ~1,100 mPa·s, measured at 20° C. in a Brookfield viscosimeter (spindle No. 4, 20 rpm), was obtained.

The mixture did not drip when applied onto wet hair dyed red. After 15 minutes processing, the hair was washed, shampooed and dried, whereupon the originally dark-blond hair color was restored.

In a comparison test a mixture was prepared of equal parts of the solution A as disclosed above and a solution B with the following composition:

| | |
|---|---|
| 10.0 (g) | citric acid |
| 0.5 | sodium lauryl sulfate |
| 0.1 | panthenol |
| 89.4 | water |
| | (pH-value: 1.7) |

The mixture of these two solutions had a pungent smell; it did not permit even distribution onto wet hair dyed red. After 15 minutes processing shampooed, complete removal of the dye and restitution of the dark-blond natural hair color could only be achieved by a further treatment with a 2.5% aqueous $H_2O_2$ solution.

What is claimed is:

1. A composition for decoloring dyed hair, consisting of two Compositions A and B being kept separately until application, whereby the Composition A comprises in an aqueous carrier about 5% to about 50% by weight, calculated to its total composition of hydrozxymethane sulfinic acid and/or an alkali salt thereof, and has an alkaline pH-value between 7.5 and 12.5, and the Composition B is present as an aqueous emulsion, containing at least one fatty or oily substance, at least one water-soluble emulsifier, and at least one perfume component, whereby a ready-to-use product with a pH-value between 2.5 and 5 is obtained upon admixing equal parts of both Compositions.

2. The composition according to claim 1, wherein the Composition A further comprises about 0.25% to 2.5% by weight, calculated to its total composition, of a thickening agent.

3. The composition according to claim 1, wherein the Composition B comprises about 0.5% to 10% by weight, calculated to its total composition, of at least one $C_{10}$–$C_{24}$-fatty alcohol, as the at least one fatty or oil substance.

4. The composition according to claim 1, wherein the Composition B comprises about 0.25% to 7.5% by weight, calculated to its total composition, of at least one anionic surfactant of the sulfate, sulfonate, carboxylate and/or alkyl phosphate type, as the at least one water-soluble emulsifier.

5. The composition according to claim 1, wherein the Composition B further comprises about 0.1% to about 1% by weight, calculated to its total composition, of the at least one perfume component.

6. The composition according to claim 1, wherein the ready-to-use mixture of the Compositions A and B has a viscosity from about 100 to about 7.500 mPa·s, measured at 20° C. in a Brookfield rotation viscosimeter.

7. A process for decoloring dyed hair, wherein a composition having a pH-value of 2.5 to 5.0, and being obtained by admixing two Compositions A and B, stored separately prior to application, is applied to wet hair, whereby the Composition A contains at least one reducing agent in an aqueous carrier and has an alkaline pH-value between 7.5 and 12.5, and the Composition B is present as an aqueous emulsion, containing at least one fatty or oily substance and at least one perfume component and having an acidic pH-value of 1 to 4, the mixture then being left to process for about five to thirty minutes, subsequently being rinsed out of the hair, the hair optionally being shampooed and dried.

8. The process according to claim 7, wherein the hair is treated with a 1% to 6% aqueous hydrogen peroxide composition subsequent to the decoloration prior to optionally being shampooed and dried.

* * * * *